United States Patent
Taheri (12) 
(10) Patent No.: US 6,293,968 B1
(45) Date of Patent: Sep. 25, 2001

(54) INFLATABLE INTRALUMINAL VASCULAR STENT

(76) Inventor: Syde A. Taheri, 268 Dan-Troy, Williamsville, NY (US) 14221

(*) Notice: Subject to any disclaimer, the term of this patent is extended or adjusted under 35 U.S.C. 154(b) by 0 days.

(21) Appl. No.: 09/422,747

(22) Filed: Oct. 21, 1999

Related U.S. Application Data (60) Provisional application No. 60/152,094, filed on Sep. 2, 1999.

(51) Int. Cl.$^7$ .................................................. A61F 2/06
(52) U.S. Cl. ........................................................ 623/1.15
(58) Field of Search .................... 623/1.25, 1.15, 623/1.16, 1.2, 1.34, 1.24; 606/194, 195, 191, 198

(56) References Cited

U.S. PATENT DOCUMENTS

| | | | |
|---|---|---|---|
| 3,868,986 | 3/1975 | Alfidi et al. | 128/345 |
| 4,140,126 | 2/1979 | Choudhury | 128/325 |
| 4,183,102 | 1/1980 | Guiset | 3/1.4 |
| 4,416,028 | 11/1983 | Eriksson et al. | 3/1.4 |
| 4,503,569 | 3/1985 | Dotter | 3/1.4 |
| 4,512,338 | 4/1985 | Balko et al. | 128/1 |
| 4,994,071 | 2/1991 | MacGregor | 606/194 |
| 5,104,404 | 4/1992 | Wolff | 623/1 |
| 5,192,310 | 3/1993 | Herweck et al. | 623/1 |
| 5,320,100 | 6/1994 | Herweck et al. | 128/654 |
| 5,330,528 * | 7/1994 | Lazim | 623/1.25 |
| 5,370,681 | 12/1994 | Herweck et al. | 623/1 |
| 5,370,691 | 12/1994 | Samson | 623/12 |
| 5,382,261 | 1/1995 | Palmaz | 606/158 |
| 5,411,550 | 5/1995 | Herweck et al. | 623/1 |
| 5,449,373 | 9/1995 | Pinchasik et al. | 606/198 |
| 5,514,154 | 5/1996 | Lau et al. | 606/195 |
| 5,549,663 | 8/1996 | Cottone, Jr. | 623/1 |
| 5,554,180 * | 9/1996 | Turk | 606/194 |
| 5,569,295 | 10/1996 | Lam | 606/198 |
| 5,591,197 | 1/1997 | Orth et al. | 606/198 |
| 5,603,721 | 2/1997 | Lau et al. | 606/195 |
| 5,649,978 * | 7/1997 | Samson | 623/1.25 |
| 5,697,971 | 12/1997 | Fischell et al. | 623/1 |
| 5,728,131 | 3/1998 | Frantzen et al. | 606/194 |
| 5,733,303 | 3/1998 | Israel et al. | 606/198 |
| 5,735,893 | 4/1998 | Lau et al. | 623/1 |
| 5,776,161 | 7/1998 | Globerman | 606/194 |
| 5,776,183 | 7/1998 | Kanesaka et al. | 623/1 |
| 5,782,789 | 7/1998 | Herweck et al. | 602/52 |
| 5,800,515 | 9/1998 | Nadal et al. | 623/1 |
| 5,810,872 | 9/1998 | Kanesaka et al. | 606/198 |
| 5,827,321 | 10/1998 | Roubin et al. | 606/195 |
| 5,836,964 | 11/1998 | Richter et al. | 606/194 |
| B1 4,733,665 | 1/1994 | Palmaz | 606/108 |

* cited by examiner

Primary Examiner—Gary Jackson
Assistant Examiner—Kevin Truong

(57) ABSTRACT

The present invention describes an inflatable intraluminal vascular stent which incorporates fine conduits of synthetic material in a meshwork like structure forming a tubular vascular prosthesis. The conduits provide for inflating and deflating the meshwork structure to deploy the stent, adjust its supporting force and for repositioning or removing the stent, if needed. Accordingly, the present invention includes a method for repairing a treatment zone in a vasculature and the like by positioning the inflatable intraluminal vascular stent bridging the treatment zone. Following insertion of the stent into the vasculature spanning the treatment zone, the meshwork structure is inflated to expand the stent against the vasculature wall. Importantly, the inflation pressure is controllable to regulate the supporting force of the stent as it conforms to the shape of the vasculature.

19 Claims, 6 Drawing Sheets

INFLATABLE INTRALUMINAL VASCULAR STENT

CROSS-REFERENCE TO RELATED APPLICATION

The present application claims priority based on provisional application Ser. No. 60/152,094, filed Sep. 2, 1999.

BACKGROUND OF THE INVENTION

1. Field of the Invention

The present invention generally relates to the treatment of arterial disease including, for example, an abdominal aortic aneurism or occlusive disease of an artery. More particularly, the present invention relates to an improved method for treating arterial disease using a novel intraluminal vascular stent formed of a meshwork of inflatable conduits. This construction provides for readily deploying the stent and for repositioning it should the stent not be initially deployed in the most optimum position in the vasculature.

2. Prior Art

The prior art describes the treatment of arterial disease by various surgical techniques, some involving the use of stents and grafts. For example, it is well known to interpose a stent within a diseased portion of the human vasculature to prop open and support the vasculature and provide unhindered fluid flow there through. Conventional stents are made of stainless steel wire, Nitinol wire and the like constructed in a meshwork form. Such stents are balloon or self-expandable inside an arterial lumen to provide for supporting and strengthening the walls of a stenotic or occluded artery. Similarly, it is well known in the prior art to use a graft in conjunction with a stent to repair damaged portions of the aorta or other arteries. Grafts, comprised of hollow tubes of prosthetic material such as Dacron, are normally inserted within the walls of a damaged artery and can be deployed into position through the use of a stented balloon catheter, thereby ensuring blood flow and reducing the risk of an aneurysm rupturing.

One of the problems with current stent designs is that it is difficult to control the supporting force which they exert against the vasculature side wall. Although the inflation pressure of the balloon catheter can be controlled, once the balloon is deflated and removed leaving the deployed stent in place, the force of the stent supporting the vasculature wall can change over time. Eventually, it is possible that a conventional wire mesh stent could become fatigued and bend and fracture to the extent that the supporting force it exerts is less than desirable to maintain open and unhindered flow through the vasculature. Conventional practice is to re-enter the treatment zone with a balloon catheter which is moved inside the relaxed stent and inflated to re-position the stent against the vasculature side wall. If the stent has relaxed to the point that it no longer sufficiently supports the vasculature wall, it must be removed and replaced.

U.S. Pat. Nos. 4,183,102 to Guiset and 5,370,691 to Samson describe inflatable devices for supporting the vasculature. However these devices do not provide a meshwork of intersecting conduits as in the present invention. Guiset disclosed a plurality of hollow toroidal sleeves while Samson relates to a helically wound polymeric tubing. These devices do not provide for lateral flow at the junction of two arteries, for example.

The present invention solves the drawbacks of the prior art by providing a novel inflatable intraluminal vascular stent or stented graft and method for treating vasculature diseases. The inflatable characteristic of the present stent means that the supporting force exerted by the stent will not change. Also, the present inflatable stent is selectively deflatable for repositioning should it later be determined that the stent is not positioned in the most desirable location within the vasculature.

SUMMARY OF THE INVENTION

The present inflatable intraluminal vascular stent incorporates fine conduits of synthetic material in a meshwork like structure forming a tubular vascular prosthesis. The conduits provide for inflating and deflating the meshwork structure to deploy the stent, adjust its force and for repositioning or removing the stent, if needed. Accordingly, the present invention includes a method for repairing a treatment zone in a vasculature and the like by positioning the inflatable intraluminal vascular stent bridging the treatment zone. Following insertion of the stent into the vasculature spanning the treatment zone, the meshwork structure is inflated to expand the stent against the vasculature wall. Importantly, the inflation pressure is controllable to regulate the supporting force of the stent as it conforms to the shape of the vasculature.

These and other aspects and advantages of the present invention will become increasingly more apparent to those skilled in the art by reference to the following description and the accompanying drawings.

DETAILED DESCRIPTION OF THE INVENTION

Figure 1A:
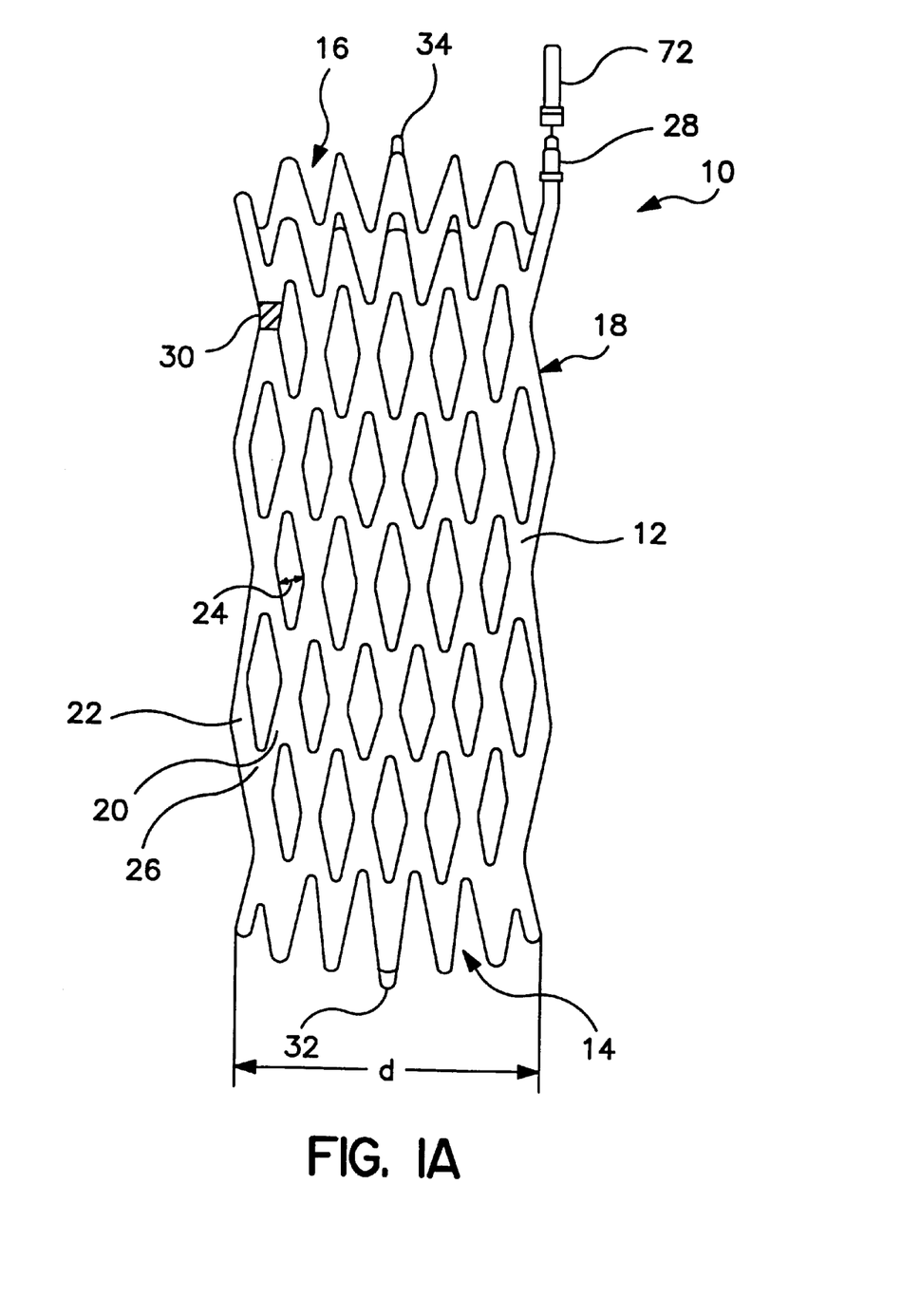
FIG. 1A is a perspective view of one embodiment of an inflatable intraluminal vascular stent 10 according to the present invention in a deflated condition.
Figure 1B:
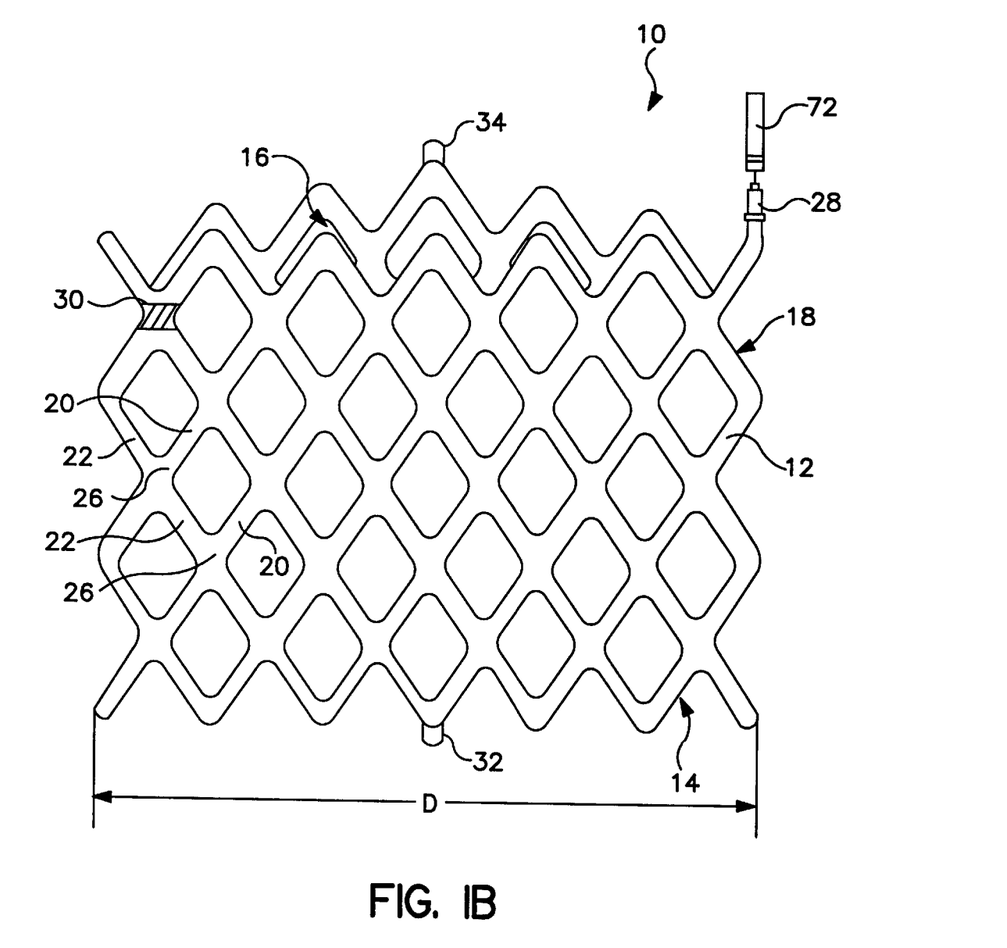
FIG. 1B is a perspective view of the stent 10 shown in FIG. 1A in an inflated condition.
Figure 2A:
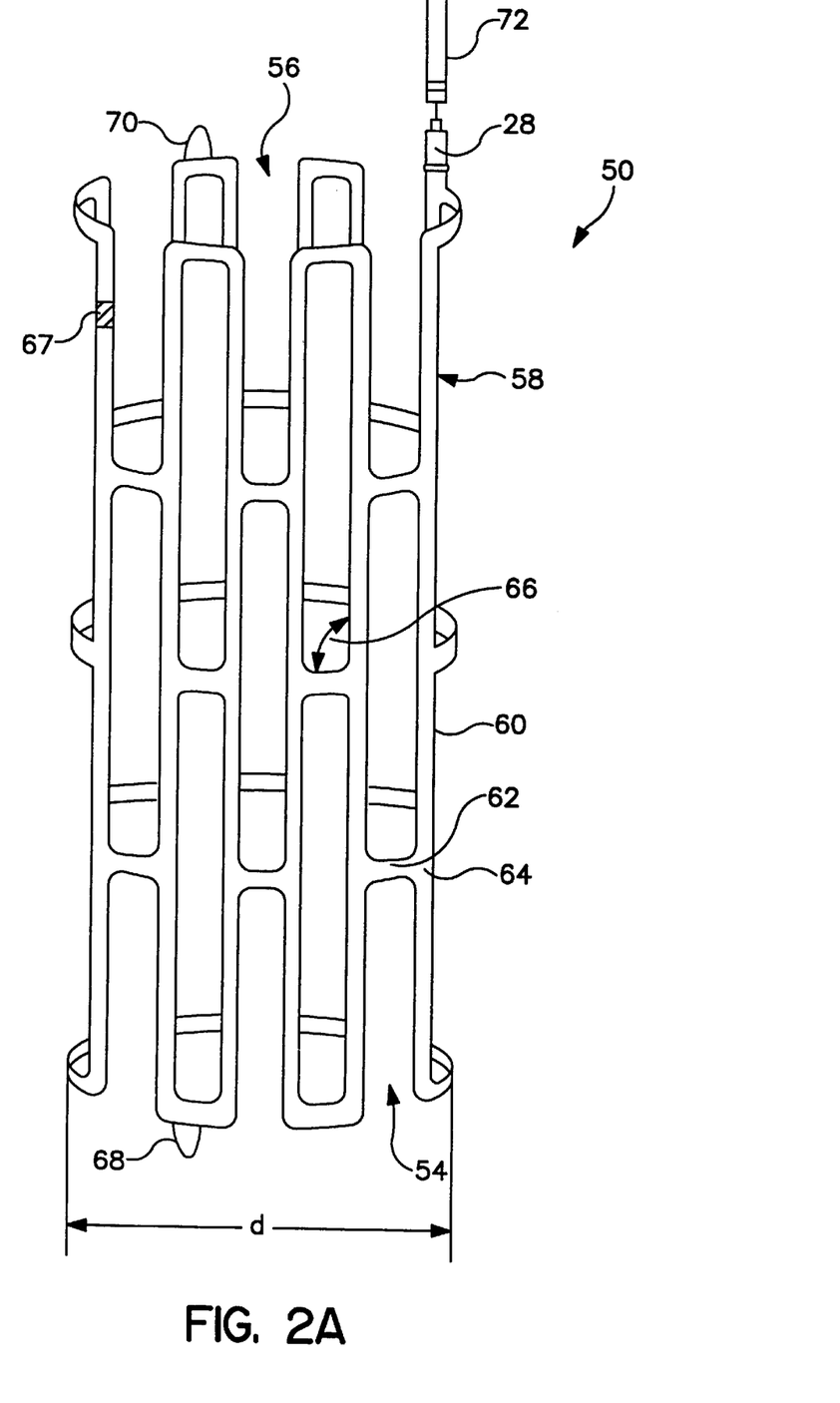
FIG. 2A is a perspective view of a second embodiment of an inflatable intraluminal vascular stent 50 according to the present invention in a deflated condition.
Figure 2B:
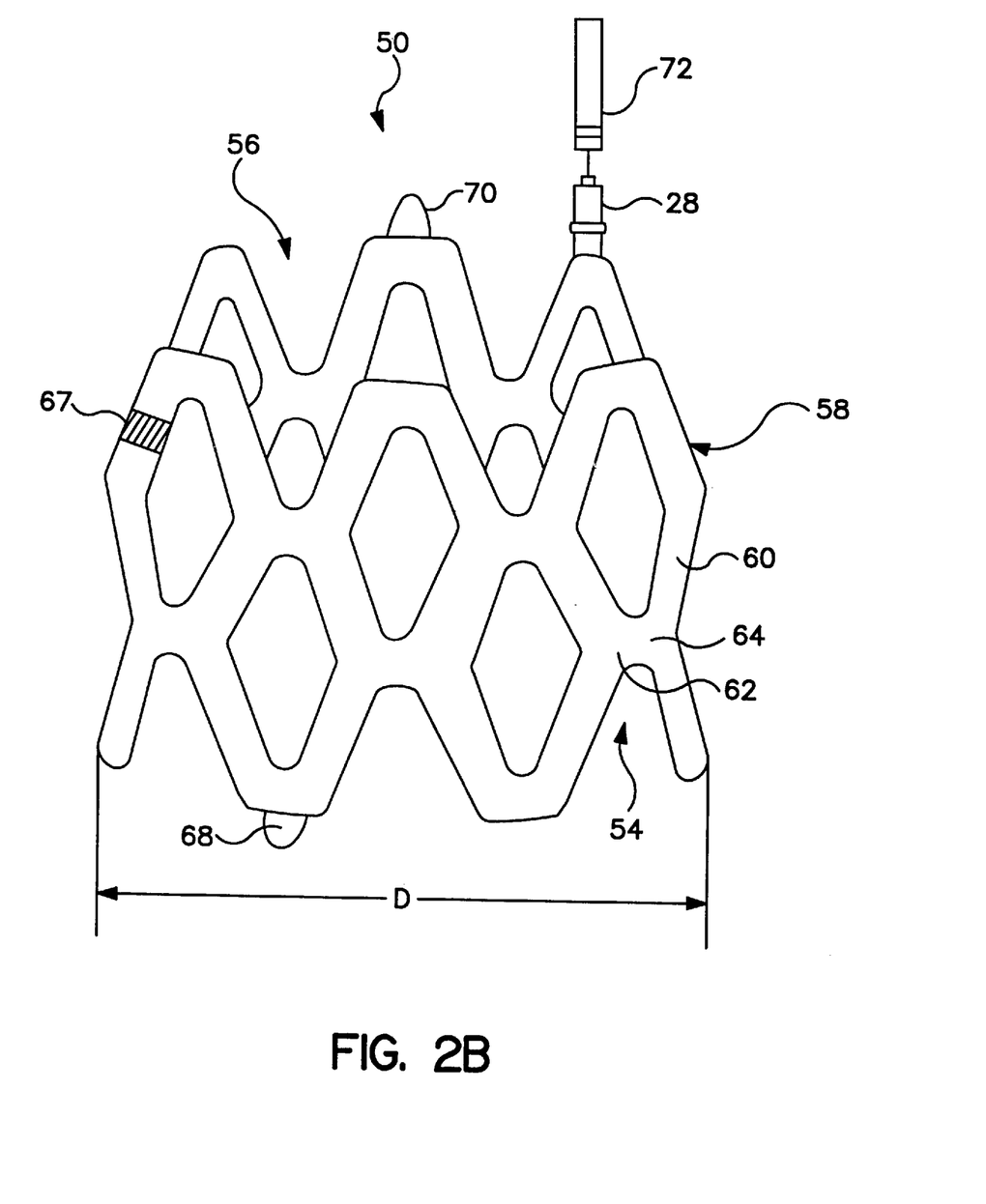
FIG. 2B is a perspective view of the stent 50 shown in FIG. 2A in an inflated condition.

Turning now to the drawings, FIGS. 1A and 1B illustrate one exemplary embodiment of an inflatable intraluminal vascular stent 10 comprising a tubular shaped prosthesis 12 for a body passageway and FIGS. 2A and 2B show another embodiment of an inflatable intraluminal vascular stent 50 comprising a tubular shaped prosthesis 52, both according to the present invention. It should be understood that the terms "inflatable intraluminal vascular stent" and "inflatable prosthesis" are interchangeably used to some extent in describing the present invention, insofar as the methods, apparatus, and structures of the present invention may be utilized not only in connection with an inflatable intraluminal vascular stent for expanding partially occluded segments of a blood vessel or a body passageway, but may also be utilized as an inflatable prosthesis for many other types of body passageways. For example, the inflatable prostheses 12, 52 may also be used for such purposes as: (1) supportive stent placement within blocked arteries opened by transluminal recanalization, but which are likely to collapse in the absence of an internal support; (2) similar use following catheter passage through mediastinal and other veins occluded by inoperable cancers; (3) reinforcement of catheter created intrahepatic communications between portal and hepatic veins in patients suffering from portal hypertension; (4) supportive stent placement of narrowing of the esophagus, the intestine, the ureters, the urethra; and (5) supportive stent reinforcement of reopened and previously obstructed bile ducts. Accordingly, the term "intraluminal vascular stent" encompasses use for expanding the lumen of a body passageway and the term "body passageway" encompasses any duct within the human body, such as those previously described, as well as any vein, artery, or blood vessel within the human vasculature.

FIGS. 1A and 1B show one embodiment of a stent 10 according to the present invention as a tubular shaped prosthesis 12 including first and second ends 14 and 16 and an outer wall surface 18 disposed between the ends. Preferably, the wall surface 18 is formed by a plurality of intersecting elongate members 20 and 22 of a conduit-shaped synthetic material. In that respect and with reference to the orientation of FIGS. 1A and 1B, the prosthesis 12 comprises the plurality of parallel elongate members 20 disposed in an orientation running generally south-west to north-east from the first end 14 to the second end 16 of the stent 10, and the plurality of parallel elongate members 22 disposed in an orientation running generally south-east to north-west from the first end 14 to the second end 16 of the stent 10.

Figure 3:
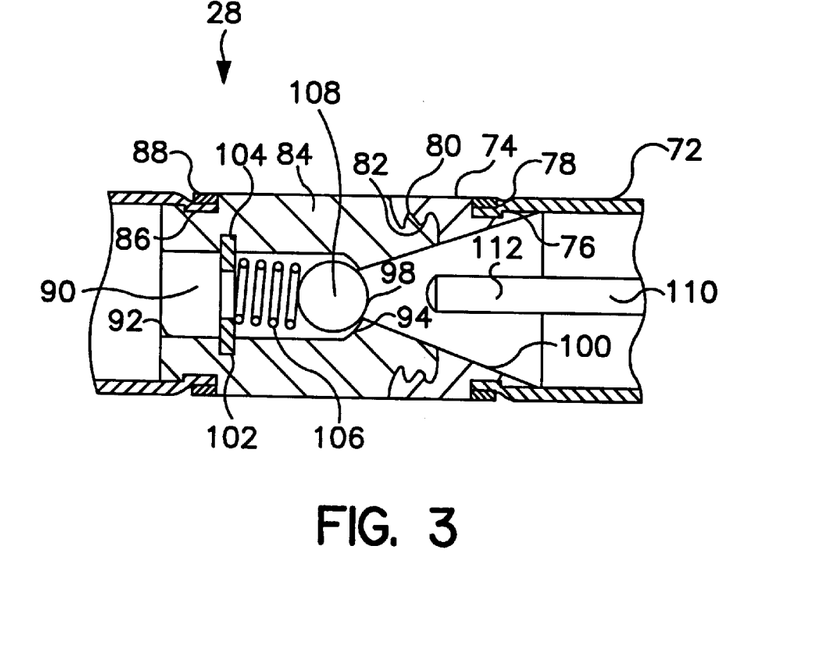
FIG. 3 is a partial cross-sectional view of the fill port 28 for the stent 10, 50 and the mating fitting 84 for the inflation conduit 72.

In the deflated condition, the conduit-shaped elongate members 20 and 22 intersect with one another at acute angles designated 24 in FIG. 1A, intermediate the first and second ends 14 and 16. This intersecting construction is shown, for example, at junctions 26. In an alternate embodiment of the present invention, the plurality of elongate members 20 and 22 do not necessarily have fluid flow communication with one another at each of their intersections 26. Instead, the outer surface of each of them are fixedly secured to one another at their intersections by ultrasonic welding, gluing and the like. What is important is that each of the plurality of elongate members 20 and 22 have fluid flow communication from a fill port 28, which is shown in FIG. 3 and will be described in greater detail hereinafter.

FIGS. 1A and 1B also show an optical radiopaque marker 30 secured to the stent 10. The radiopaque marker 30 is optional, but is necessary to determine the position of the stent in the vasculature during deployment. The marker 30 may be any suitable radiopqaue material, preferably metal. Materials such as the platinum series of metals (platinum, palladium, etc.) and gold, silver, and tantalum may be used as the marker 30. Certain stainless steels are also suitable for use as the marker. It should also be understood that the marker 30 can have various shapes and sizes and should not be limited to that shown.

Also shown in FIG. 1A, the tubular shaped prosthesis 12 has a first diameter, d, which permits intraluminal delivery of the prosthesis 12 into a body passage (not shown). With reference to FIG. 1B, upon the application of an inflating force to the conduit construction of the intersecting elongate members 20 and 22, the tubular shaped prosthesis 12 inflates to a second diameter, D. The second diameter D is variable in size and dependent upon the force of the medium inflated into the intersecting elongate members 20 and 22 of the tubular shaped prosthesis 12

The elongate members 20 and 22 forming the outer wall surface 18 of the tubular shaped prosthesis 12 may be of any suitable synthetic polymeric material which is inflatable and compatible with the human body and with bodily fluids with which the vascular graft or prosthesis 12 may come into contact. In that respect, the elongate members 20 and 22 must be made of a synthetic material which has the requisite strength and elasticity characteristics to permit the tubular shaped prosthesis 12 to be inflated from the configuration shown in FIG. 1A to the configuration illustrated in FIG. 1B and further to permit the tubular shaped prostheses 12 to retain its inflated configuration providing the enlarged diameter D. Exemplary synthetic polymeric materials for the stent 10 include high-density polyethylene, low-density polyethylene, and polypropylene, as well as interpolymers and block copolymers of these polyolefins. Other polymers such as polyacrylonitrile, polyethylene terephthalate, polybutylene terephthalate, silicones, natural and synthetic rubbers and polytetrafluoroethylene are also suitable materials. Further, it is within the scope of the present invention to provide an inflatable stent as a hybrid of these materials. For example, it may be desirable to provide the stent made of two of the materials so that different portions of the stent inflate at different rates.

Preferably, the elongate members 20 and 22 are fabricated from PTFE having a cylindrical cross-section. The elongate members 20 and 22 can, of course, have other cross-sectional configurations, such as triangular, square, rectangular, hexagonal, etc.

Finally, the prosthesis 12 is provided with loops 32 and 34 at the respective first and second ends 14 and 16. The loops 32 and 34 provide for positioning the prosthesis 12 at a treatment zone in the vasculature using the apparatus and method set forth in U.S. Pat. No. 5,948,017 to Taheri. This patent is incorporated herein by reference.

FIGS. 2A and 2B show another preferred embodiment of an inflatable intraluminal vascular stent 50 comprising a tubular shaped prosthesis 52 having first and second ends 54 and 56 and an outer wall surface 58 disposed between the ends. The outer wall surface 58 is formed of a plurality of longitudinal members 60 intersecting with lateral numbers 62, both of a conduit-shaped synthetic material. In the deflated condition, the conduit-shaped elongate members 60 and 62 intersect with one another at right angle junctions, designated 64 in FIG. 2A. The connecting members 60 and 62 are of a conduit-shaped material in fluid flow communication with each other and with a fill port 28. The fill port 28, which is similar to that shown in FIGS. 1A and 1B, is described in detail hereinafter with respect to FIG. 3 and provides for inflating the connecting members 60 and 62 of the stent 50 having a deflated diameter d to provide the expanded stent configuration shown in FIG. 2B having the inflated diameter D.

As with the prosthesis 10 shown in FIGS. 1A and 1B, prosthesis 50 is provided with a radiopaque marker 67 and with loops 68 and 70 at its respective ends 54 and 56 for positioning the prosthesis in the vasculature according to U.S. Pat. No. 5,948,017 to Taheri.

It should be pointed out that the prosthesis configurations illustrated in FIGS. 1A, 1B, 2A and 2B are only illustrative. In that respect, FIGS. 1A and 1B are provided to illustrate that the present invention covers stents having conduit-shaped members meeting each other at an acute angle in the deflated condition and FIGS. 2A and 2B are provided to illustrate that the present invention also covers stents having conduit-shaped members meeting each other at right angles in the deflated condition. Accordingly, stents 10 and 50 are illustrative and inflatable prosthesis according to the present invention can have a myriad of configurations that are only limited by the imagination of those skilled in the art. For example, U.S. Pat. Nos. B1 4,733,665, 4,994,071, 5,104, 404, 5,382,261, 5,449,373, 5,514,154, 5,549,663, 5,569,295, 5,591,197, 5,603,721, 5,697,971, 5,728,131, 5,733,303, 5,735,893, 5,776,161, 5,776,183, 5,800,515, 5,810,872, 5,827,321 and 5,836,964 are illustrative of various alternative shapes of prosthesis devices which can be made of conduit-material, instead of the wire material described in the respective patents, to provide an inflatable prosthesis according to the present invention.

FIGS. 1A, 1B, 2A and 2B show the respective stents 10 and 50 having an inflation conduit 72 connectable to the fill port 28 for inflating the stents. As shown in greater detail in FIG. 3, the inflation conduit 72 is a cylindrically shaped member having a threaded fitting 74 at its distal end. The inflation conduit 72 is made of a synthetic material that is flexible enough to travel through the vasculature to the stents 10, 50 positioned at a treatment zone in the vasculature. In the alternative, the inflation conduit is connected to the stent as the stent is being deployed to the treatment zone.

The threaded fitting 74 is a female shaped member connected to a reduced diameter portion 76 of the distal end of the inflation conduit 72 by a hose clamp 78 and the like. The fitting 74 is provided with double threads 80 that threadingly mate with the double threads 82 of a male fitting 84 secured to a reduced diameter portion 86 of the stent 10, 50 by a hose clamp 88. The male fitting 84 has an internal bore 90 comprising a cylindrical shaped portion 92 leading to a dome-shaped restriction 94. The dome-shaped restriction 94 communicates with a frusto-conical portion 96 forming a seat 98. The frusto-conical portion 96 tapers outwardly from the seat 98 to the threaded end of the fitting 84. The female fitting 74 is provided with an internal frusto-conical bore 100 that tapers outwardly from the threads 80 towards the inflation conduit 72. When the female fitting 74 is threadingly mated to the male fitting 84 the respective frusto-conical portions 96 and 100 align with each other. The male fitting 84 is also provided with an annular groove 102 intermediate the length of the cylindrical shaped portion 92 of the bore 90. The annular groove 102 is of a greater diameter than the cylindrical portion 92 and supports a snap-ring 104 that confines a coil spring 106 biasing a ball check valve 108 against the seat 98. Preferably the ball 108 is of deformable synthetic material to seal against the seat 98 to thereby seal the inflatable stent 10, 50.

Figure 4:
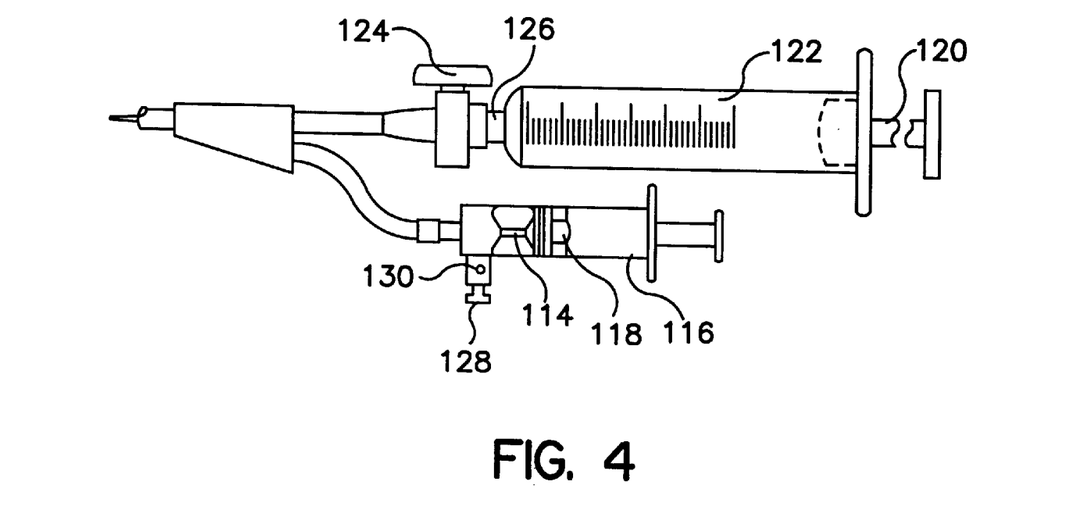
FIG. 4 is a perspective view of a release plunger 116 for opening the fill port 28 and a pump 122 for inflating the stent.

To inflate the stent 10, 50, the female fitting 74 at the end of the inflation conduit 72 is threadingly mated to the male fitting 84. Those skilled in the art will readily understand that the inflation conduit 72 could be provided with male threads and the stent fitting 84 with female threads without departing from the spirit and scope of the present invention. The inflation conduit 72 supports an internal release wire 110 having its distal end 112 residing in the frusto-conical sections 96 and 100 and its proximal end 114 disposed in a release plunger 116 (FIG. 4).

The release plunger 116 has a piston 118 connected to the release wire 110 for moving the wire towards and away from the ball check valve 108. When the release wire 110 contacts the ball check valve 108, it overcomes the biasing force of spring 106 to open communication between the inflation tube 72 and the stent 10, 50. With the check valve 108 opened, an inflation plunger 120 of an inflation pump 122 is actuated to fill an inflation medium into the stent 10, 50. This is done by first opening a shut-off valve 124 and moving the plunger 120 toward the opened check valve 108 to move the inflation medium into the stent 10, 50. The inflation medium can comprise a gaseous material such as carbon dioxide, air, a flowable gelatinous material, a metal powder, water or similar fluid and the like. In that manner, the prosthesis is radially and laterally expanded from its collapsed or deflated diameter d to its inflated diameter D. The second diameter D is variable and controlled by the amount of inflation medium flowed into the prosthesis.

When the stent 10, 50 is properly inflated, the piston 118 of the release plunger 116 is moved away from the stent 10, 50 to move the release wire 110 back into the female fitting 74. This enables the ball check valve 108 to seal against the seat 98 to close communication into and out of the stent. The shut-off valve 124 is closed and if desired, the pump 122 is disconnected from the inflation conduit 72 by coupling 126.

Should it be determined that the stent has been inflated too much, the plunger 120 is actuated to move the release wire 110 to open the check valve 108 as has previously been described. A needle valve 128 on the release plunger 116 is then actuated to open communication with the inflation conduit 72 to bleed off a quantity of the inflation medium through a vent opening 130 of the release plunger 116. That way, the inflation medium is removed from the stent to deflate it, as needed. This could occur if it is later determined after deployment that the stent is in a position in the vasculature that is not optimum, or if the stent is initially over inflated.

At such time as the prosthesis is completely inflated to support the vasculature, the inflation conduit 72 is rotated in the opposite direction from that used to connect the inflation conduit to the stent 10, 50. The inflation conduit 72 is withdrawn from the vasculature and the vasculature is then closed in the normal manner.

Figure 5:
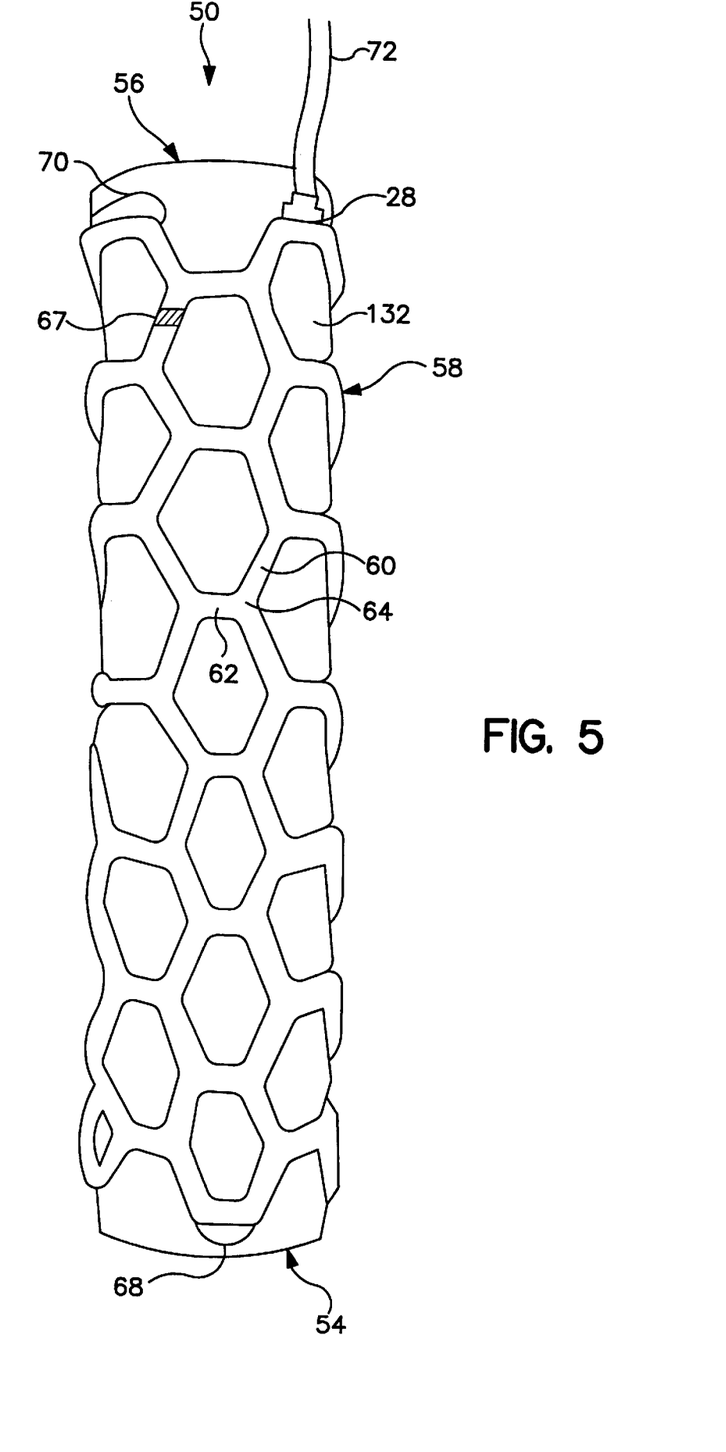
FIG. 5 is a perspective view of the stent of FIGS. 2A and 2B secured to a graft 132 according to the present invention.

FIG. 5 is a perspective view showing that it is also within the scope of the present invention to combine the stent 50 with a graft 132. The graft 132 is a hollow tube of prosthetic material such as Dacron, that is secured to the stent 50 such as by sewing, gluing and the like. The graft further helps to ensure blood flow through the vasculature and to reduce the risk of an aneurysm rupturing, as is well known to those skilled in the art.

It is intended that the foregoing description be only representative of the present invention and that the present invention be only limited by it hereinafter appended claims.

What is claimed is:

1. A stent for a treatment zone in a body passageway, which comprises:
   a) at least one tubular shaped prosthesis made from a meshwork of intersecting inflatable conduit members and plural openings extending traverse to the inflatable conduit members, the tubular shaped prosthesis having an outer surface, an interior and first and second open ends, and further having a first diameter which permits intraluminal delivery of the at least one tubular shaped prosthesis into the body passageway; and
   b) a valve in fluid flow communication with the meshwork to provide for inflation of the prosthesis to a second diameter greater than the first diameter to thereby support a portion of the body passageway at the treatment zone.

2. The stent of claim 1 wherein the meshwork is of a plurality of intersecting conduit members that are in fluid flow communication with each other intermediate the first and second ends.

3. The stent of claim 1 wherein the meshwork is of at least first and second conduit members that intersect with each other at an acute angle.

4. The stent of claim 1 wherein the meshwork is of at least first and second conduit members that intersect with each other at right angles with the prosthesis in a deflated condition.

5. The stent of claim 1 wherein the meshwork is of conduit members of a synthetic polymeric material.

6. The stent of claim 5 wherein the synthetic polymeric material is selected from the group consisting of polyethylene, polypropylene, polyacrylonitrite, polythylene terephthalate, polybutylene terephthalate, polytetrafluorothylene, silicones, natural and synthetic rubber, and mixtures thereof.

7. The stent of claim 1 wherein the valve is a check valve for opening and closing communication with the meshwork.

8. The stent of claim 1 wherein the prosthesis includes a radiopaque marker.

9. The stent of claim 1 wherein the prosthesis is inflatable by moving an inflation material selected from the group consisting of carbon dioxide, air, a flowable gelatinous material and a metallic powder into the prosthesis.

10. A method for supporting a vasculature side wall at a treatment zone, comprising the steps of:
  a) providing at least one tubular shaped prosthesis made from a meshwork of intersecting inflatable conduit members and plural opening extending traverse to the inflatable conduit members, the tubular shaped prosthesis having an outer surface, an interior and first and second open ends, and further having a first diameter which permits intraluminal delivery of the at least one tubular shaped prosthesis into the body passageway and a valve in fluid flow communication with the meshwork to provide for inflation of the prosthesis;
  b) moving the prosthesis to the treatment zone in the vasculature;
  c) opening the valve and introducing an inflation medium into the prosthesis to provide the prosthesis having a second diameter greater than the first for supporting the vasculature side wall; and
  d) closing the valve.

11. The method of claim 10 wherein the meshwork has a plurality of intersecting conduit members that are in fluid flow communication with each other intermediate the first and second ends.

12. The method of claim 10 wherein the meshwork has at least first and second conduit members that intersect with each other at an acute angle.

13. The method of claim 10 wherein the meshwork has at least first and second conduit members that intersect with each other at right angles with the prosthesis in a deflated condition.

14. The method of claim 10 wherein the meshwork has conduit members of a synthetic polymeric material.

15. The method of claim 10 wherein the prothesis has a radiopaque marker.

16. A kit for positioning a prosthesis in a treatment zone in a vasculature of a human body, the kit comprising:
  a) at least one tubular shaped prosthesis made from a meshwork of intersecting inflatable conduit members and plural interstitial passageway openings between non-intersecting portions of the inflatable conduit members, the tubular shaped prosthesis having an outer surface, an interior and first and second open ends, and further having a first diameter which permits intraluminal delivery of the at least one tubular shaped prosthesis into the body passageway;
  b) a valve in fluid flow communication with the meshwork to provide for inflation of the prosthesis to a second diameter greater than the first diameter to thereby support a portion of the body passageway at the treatment zone; and
  c) an inflation conduit matable with the valve for inflating the prosthesis.

17. The kit of claim 16 wherein one of the valve and the inflation conduit is provided with a threaded female fitting that is matable with a threaded male fitting of the other of the valve and the inflation conduit.

18. The kit of claim 16 wherein the valve of the prosthesis comprises a ball check valve and the inflation conduit has an internal wire that is movable towards the ball check valve to open fluid flow communication with the prosthesis and movable away from the ball check valve to close communication with the prosthesis.

19. The kit of claim 16 including a release device for removing inflation material from the prosthesis.

* * * * *